United States Patent [19]

Robins et al.

[11] Patent Number: 4,861,873

[45] Date of Patent: Aug. 29, 1989

[54] 8-CHLOROADENOSINE 3', 5'-CYCLIC MONOPHOSPHATE PREPARATIONS

[75] Inventors: Roland K. Robins; Ganapathi R. Revankar, both of Irvine; Yu-an Chang, Costa Mesa, all of Calif.

[73] Assignee: Nucleic Acid Research Institute, Costa Mesa, Calif.

[21] Appl. No.: 136,407

[22] Filed: Dec. 21, 1987

[51] Int. Cl.[4] .................... C07H 19/20; C07H 19/00
[52] U.S. Cl. ........................................ 536/27; 536/28; 536/29
[58] Field of Search .............................. 536/27, 28, 29

[56] References Cited

PUBLICATIONS

Brown, "Chemical Reactions of Polynucleotides and Nucleic Acids", Ch. 1, vol. II, Basic Principles Nucleic Acid Chem., Ts'O ed., 1979, pp. 32–33.
Kochert Kov et al., Organic Chemistry of Nucleic Acids, Part B, pp. 272–274.
Katsaros et al, Fed. Europ. Biochem. Societies, vol. 223(1), pp. 97–103, 1987.
Niles et al., J. Biol. Chem., vol. 254(11), pp. 4324–4326, 1979.
Cancergram of the International Cancer Research Data Bank, Series CB14, #80/03. Mar. 1980.
Abstract #62, T. S. Cho-Chung, et al., Proceedings of ASCO vol. 6, Mar. 1987.
Abstract #180, G. Tortora et al., Proceedings of AACR, vol. 28, Mar. 1987.
Abstract #930, D. Karsaros et al., Proceedings of AACR, vol. 28, Mar. 1987.
Abstract #1323, Y. S. Cho-Chung et al, Proceedings of AACR, vol. 28, 1987.
Muneyama et al, J. Char. Nucleosides Nucleotides, 1(1), 55–60 (1974).
Ruy et al., J. Org. Chem., vol. 46, No. 13 (1981).

*Primary Examiner*—Johannie R. Brown
*Assistant Examiner*—L. Eric Crane
*Attorney, Agent, or Firm*—Herb Boswell

[57] ABSTRACT

The compound 8-Chloroadenosine 3',5'-cyclic phosphate is used to treat malignant tumors in warm blooded animals. Two novel single step syntheses of 8-chloroadenosine 3',5'-cyclic phosphate and other related adenine and adenosine compounds from corresponding adenosine 3', 5'-cyclic phosphate and other respective related adenosine compounds are disclosed.

12 Claims, No Drawings

8-CHLOROADENOSINE 3', 5'-CYCLIC MONOPHOSPHATE PREPARATIONS

BACKGROUND OF INVENTION

This invention is directed to treating malignant tumors in vivo utilizing the compound 8-chloroadenosine 3',5'-cyclic phosphate. This compound and other related adenine and adenosine compounds are prepared by two novel syntheses utilizing hydrogen chloride and m-chloroperoxybenzoic acid in a suitable solvent in the first synthesis and N-chlorosuccinamide and acetic acid in a suitable solvent in the second synthesis.

While the arsenal of chemotherapeutic agents for treating neoplastic diseases includes a number of clinically useful agents, control of malignant tumors in warm blooded animals still remains a much sought after goal.

In a study reported from the People's Republic of China but not confirm elsewhere, 8-bromoadenosine 3',5'-cyclic phosphate was noted as inhibiting the solid form of uterine tumor 14 Ehrlich carcinoma, sarcoma-180 and reticulum-cell sarcoma in mice. An abstract of this study appeared in a Cancergram of the International Cancer Research Data Bank, Series CB14 Number 80/03, March 1980, published by the United States Department Health, Education and Welfare National Institute of Health, National Cancer Institute. In contrast to this report, in other studies 8-bromoadenosine 3',5'-cyclic phosphate has been found to be inactive as an antitumor agent in cell culture.

Contemporaneously with the above report, Y. S. Cho-chung, *J. Cyclic Nucleotide Res.* 6: 163, 1980, reported certain investigative studies on an antagonistic interaction between estrogen and adenosine 3',5'-cyclic monophosphate (hereinafter alternately referred to as cAMP) and what role this might have in the control of growth of hormone-dependent mammary tumors.

In studying the effects of mediated control of tumor growth by adenosine 3',5'-cyclic phosphate, Cho-chung has elucidated that cAMP functions by binding to a cAMP receptor protein which has two different cAMP binding sites. The cAMP receptor protein is a regulatory subunit of a cAMP dependent protein kinase. There apparently is site selectivity in binding to one or the other of two sites. This activity can thus be described as site 1-selectivity and site 2-selectivity.

In view of the inability of current cancer chemotherapeutics to successfully control all neoplastic diseases, it is evident that there exists a need for new and additional cancer chemotherapeutic agents. Further there exist a need for new and better preparative procedures for the syntesis of such new and additional cancer chemotherapeutic agents.

8-chloroadenosine 3',5'-cyclic phosphate was first reported by inventor R. K. Robins of this invention and his other co-authors in K. Muneyama et al, *J. Charbohyd. Nucleosides Nucleotides*, 1, 55, 1974. It has now been found that 8-chloroadenosine 3',5'-cyclic phosphate (hereinafter alternately also identified as 8-chloro cAMP), exhibits such significant antitumor activity so as to be useful as an antitumor agent in vivo. Further, two novel preparative synthesis yield 8-chloroadenosine compounds such as 8-chloroadenosine 3',5'-cyclic phosphate directly from respective adenosine precursors.

BRIEF DESCRIPTION OF THE INVENTION

The present invention relates to the use of 8-chloroadenosine 3'5'-cyclic phosphate (8-chloro cAMP) in treating malignant tumors in warm blooded animals. According to this invention the antitumor properties of 8-chloroadenosine 3',5'-cyclic phosphate are achieved by administering to a warm blooded animal an effective amount of a pharmaceutical composition containing 8-chloroadenosine 3',5'-cyclic phosphate or pharmaceutically acceptable salts thereof as the active compound in at least 0.1% by weight based on the total weight of the composition.

For use in pharmaceutical compositions of the invention a pharmaceutical carrier would be utilized. Preferredly the carrier would be chosen to allow for administration of a suitable concentration of 8-chloroadenosine 3',5'-cyclic phosphate either by oral administration, ophthalmic administration, topical administration, suppository administration or by suitable injection as a solution or suspension into the affected warm blooded animal. The dose and choice of administration of 8-chloroadenosine 3',5'-cyclic phosphate of the invention would be dependent upon the host harboring the malignant tumor, the type of tumor and the tumor site. For injection, 8-chloroadenosine 3',5'-cyclic phosphate of the invention could be administered intraveneously, intramuscularly, intracerebrally, subcutaneously or intraperitoneally. Further, for facilitating the use of 8-chloroadenosine 3',5'-cyclic phosphate, a physiologically accepted salt, as for instance the sodium, potassium or ammonium salt, could be used. Presently it is preferred to administer the compound by infusion.

Further, the invention includes improved processes for the preparation of 8-chloro derivatives of adenine, adenosine, adenosine 5'-monophosphate and adenosine 3',5'-cyclic phosphate and related compounds. In these improved processes 8-chloroadenine, 8-chloroadenosine, 8-chloroadenosine 5'-monophosphate and 8-chloroadenosine 3',5'-cyclic phosphate or other related adenosine compounds are prepared directly from corresponding respective adenosine precursor compounds by processes for preparing chloro compounds of the formula

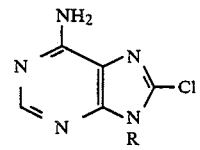

wherein R is H or

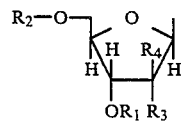

wherein $R_1$ and $R_2$ are H or

or together $R_1$ and $R_2$ are

and $R_3$ and $R_4$ are H or one of $R_3$ or $R_4$ is OH and the other is H, and pharmaceutically acceptable salts thereof which comprise the steps of:

treating a starting compound of the formula

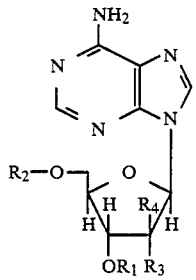

wherein $R_1$ and $R_2$ are H or

or together $R_1$ and $R_2$ are

and $R_3$ and $R_4$ are H or one of $R_3$ or $R_4$ is OH and the other is H:
either, (1) with N-chlorosuccinimide and a weak acid in a suitable solvent or (2) with hydrogen chloride and an oxidizing agent in a suitable solvent.

DETAILED DESCRIPTION OF THE INVENTION

8-Chloroadenosine 3',5'-cyclic phosphate of the invention can be prepared as was described in above referenced paper, K. Muneyama et al, *J. Carbohydr. Nucleosides Nucleotides*, 1, 55 1974, via an 8-bromo intermediate compound, however, by utilizing new and improved processes as discussed herein, 8-chloroadenosine 3',5'-cyclic phosphate and related compounds are obtained directly from respective adenosine precursors avoiding having to synthesis intermediate compounds. As such, improvements in the economy of the synthesis are obtained.

In the first of these improved processes adenosine 3',5'-cyclic phosphate is directly chlorinated to 8-chloroadenosine 3',5'-cyclic phosphate utilizing N-chlorosuccinimide and a suitable weak acid in a suitable solvent. Suitable as the weak acid is acetic acid. Alternatively formic acid or other weak organic acid might be used. In choosing the acid, consideration is given whereby the acid is of such a strength that it is sufficiently weak so as not to cleave the sugar-heterocycle glycosidic bond (the C1'-N9 bond). Suitable as the solvent are dimethylacetamide, dimethylformamide or aqueous medium.

In the second of these improved processes adenosine 3',5'-cyclic phosphate is also directly chlorinated to 8-chloroadenosine 3',5'-cyclic phosphate utilizing anhydrous hydrogen chloride and a suitable oxidizing agent such as m-chloroperoxybenzoic acid. This reaction is conduct in a suitable solvent as for example dimethylacetamide or dimethylformamide. As an alternative oxidizing agent, sodium hypochlorite can be mentioned.

Aside from the preparation of 8-chloroadenosine 3',5'-cyclic phosphate, both of these processes can be utilized to prepare 8-chloroadenosine from adenosine or 8-chloroadenosine 5'-phosphate from adenosine 5'-phosphate. Further, if the hydrogen chloride/m-chloroperoxybenzoic acid reaction is carried out in the presence of moisture, it can be utilized to prepare 8-chloroadenine from adenosine.

Additionally, these two novel processes might also be utilized to convert suitable derivatives of adenosine, adenosine 5'-phosphate, adenosine 3'-phosphate and adenosine 3',5'-cyclic phosphate, to their respective 8-chloro derivatives. Such derivatives would include the 2-deoxy-β-D-erythro-pentofuranosyl sugar derivative and the 2-β-D-arabinofuranosyl sugar derivative and might also include substituents on the purine amino group, the 2 position of the purine ring, sugar hydroxyl groups or even other heterocyclic moieties such as a deaza purine or the like.

The synthesis of 8-chloroinosine 3',5'-cyclic phosphate, 8-chloroinosine 5'-phosphate and 8-chloroinosine is facilitated utilizing these processes in that the respective 8-chloroadenosine compounds can then be directly deaminated utilizing nitrous acid to respective 8-chloroinosine derivatives. For this reaction, the nitrous acid can be generated in situ from sodium nitrite and acetic acid. Thus 8-chloroinosine and its 5'-phosphate and 3',5'-phosphate derivatives are synthesised in a straight forward two step reaction scheme.

In the following examples of the novel processes of the invention as is illustrated in scheme I, an adenosine compound, e.g. adenosine, AMP or cAMP, is directly chlorinated in the 8 position of its purine ring to an appropriate 8-chloroadenosine or adenine compound. Thus adensoine yields compounds 1 and 2, AMP yields compound 3 and cAMP yields compound 4. This is achieved using one, the other or both of the two novel processes.

One process uses hydrogen chloride and m-chloroperoxybenzoic acid in an appropriate solvent such as dimethylacetamide or dimethylforamide. The other process uses N-chlorosuccinamide and acetic acid in an appropriate solvent such as dimethylacetamide, dimethylformamide or an aqueous acetic acid. Any of the 8-chloro compounds thus formed can then be further converted in a further step to their 8-chloroinosine analogs as for instance the conversion of 8-chloroadenosine 3',5'-cyclic phosphate, compound 4, to 8-chloroinosine 3',5'-cyclic phosphate, compound 5.

In the preparative examples below, melting points were taken on a Thomas-Hoover capillary melting point apparatus or on a Haake-Buchler digital melting point apparatus and are uncorrected. Nuclear magnetic resonance ($^1$H NMR) spectra were determined at 300.1 MHz with an IBM NR300AF spectrometer. The chemical shifts are expressed in δ values (parts per million)

relative to tetramethylsilane as internal standard. Ultraviolet spectra (UV: sh=shoulder) were recorded on a Beckman DU-50 spectrophotometer. Elemental analyses were performed by Robertson Laboratory, Madison, N.J. Evaporations were carried out under reduced pressure with the bath temperature below 40° C. Thin layer chromatography (TLC) was run on silica gel 60 F-254 plates (EM Reagents). E. Merck silica gel (230-400 mesh) was used for flash column chromatography.

to give 1.44 g (85.2%) of 1: mp 305°-310° C. (dec.) [Lit. mp>300° C. (dec.)]: IR (KBr): 630 (C-Cl), 3100-3300 (NH$_2$) cm$^{-1}$: UV: $\lambda_{max}$ (pH 1) 262 nm ($\epsilon$ 8,700): $\lambda_{max}$ (pH 7) 268 nm ($\epsilon$ 7,900): $\lambda_{max}$ (pH 11) 269 nm ($\epsilon$ 8,300): $^1$H NMR (Me$_2$SO-d$_6$): $\delta$ 7.48 (br s, 2, NH$_2$), 8.10 (s, 1, C$_2$H) and 13.60 (br s, 1, N$_9$H).

EXAMPLE 2

8-Chloroadenosine (2)

Method A

SCHEME I

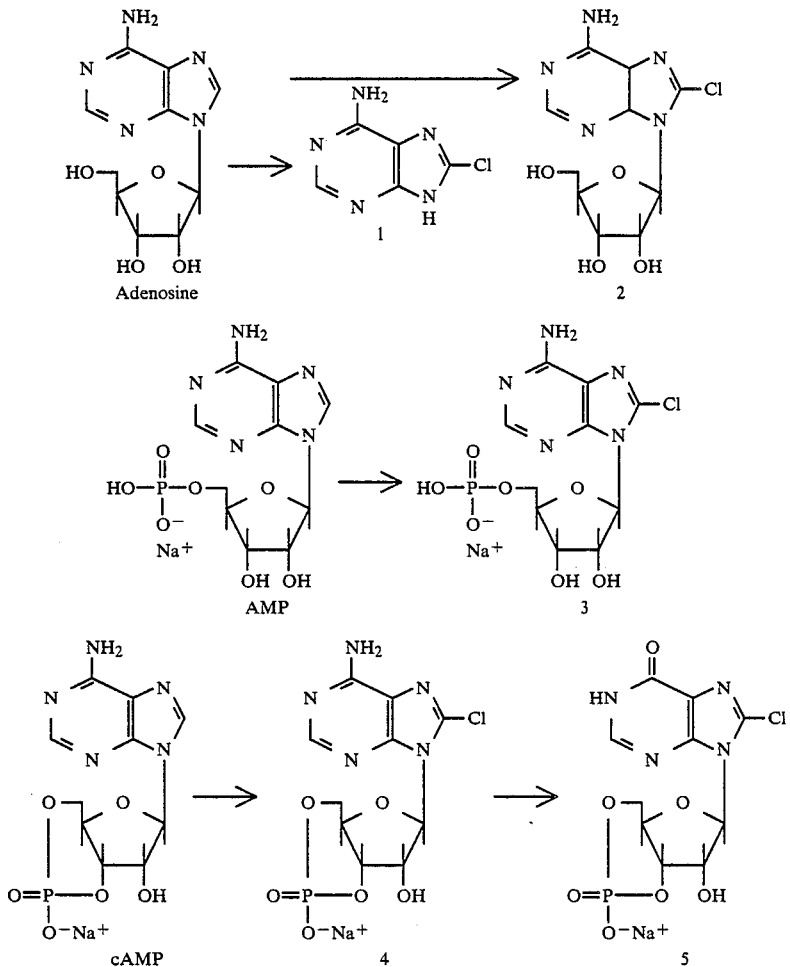

EXAMPLE 1

8-Chloroadenine (1)

To a solution of adenosine (2.67 g, 10 mmol) in DMA/HCl (0.5M, 45 mL) was added m-chloroperoxybenzoic acid (MCPBA, 3.22 g, 16 mmol 87%) and stirred at room temperature for 2.5 h. An additional portion of MCPBA (0.9 g, 5 mmol) was added and stirring continued for another 1 h. Toluene (50 mL) was added to the reaction mixture and the solvents evaporated at 60° C. under vacuo to dryness. The residue was dissolved in water (50 mL) and extracted with ether (3×50 mL). The pH of the aqueous phase was adjusted to 5 with 2N NaOH and then diluted with EtOH (100 mL). The solution was stored in the refrigerator overnight. The light yellow solid that separated was collected, washed with cold EtOH (2×25 mL) and dried To a solution of adenosine (2.67 g, 10 mmol, dried at 80° C. under vacuum) in DMA/HCl (0.5 M, 25 mL) was added rapidly solution of purified MCPBA (3.09 g, 18 mmol) in DMA (20 mL) (adenosine will precipitate out from the reaction mixture if the MCPBA solution is not added quickly). After stirring at room temperature for 2 h, additional MCPBA (0.7 g, 4 mmol) was added and the mixture was stirred for another ½ h until all the adenosine disappeared. The DMA was evaporated in vacuo and the residue was purified by HPLC on a C-18 reverse phase column using MeOH: AcOH:H$_2$O (18:1:81, v/v) to give 1.25 g (41%) of 2: mp 188°-189° C. [Lit. mp 188°-190° C.]: IR (KBr): 795 (C-Cl), 3150-3400 (NH$_2$, OH) cm$^{-1}$: UV: $\lambda_{max}$ (pH 1) 261 nm ($\epsilon$ 17,100): $\lambda_{max}$ (pH 7) 262 nm ($\epsilon$ 17,800): $\lambda_{max}$ (pH 11)

263 nm (ε 16,700): $^1$H NMR (Me$_2$SO-d$_6$): δ 5.83 (d, 1, $J_{1',2'}$=7.0 Hz, C$_{1'}$H), 7.59 (br s, 2, NH$_2$) and 8.14 (s, 1, C$_2$H).

Method B to a solution of adenosine (1.09 g, 4.1 mmol) in DMF (50 mL) and AcOH (10 mL) was added N-Chlorosuccinamide (NCS, 2.0 g, 15 mmol). The reaction mixture was stirred at room temperature for 6 days. The solvents were evaporated to dryness and the residue was purified by HPLC on a C-18 reverse phase column using MeOH:AcOH:H$_2$O (18:1:18, v/v) to give 0.8 g (65%) of 2, which was identical to the title compound prepared by Method A.

EXAMPLE 3

8-Chloroadenosine 5'-monophosphate (3)

Method A

To a solution of adenosine 5'-monophosphate (1.3 g, 3.5 mmol) in dry DMF (75 mL, distilled over CaH$_2$) was added dropwise a solution of DMF saturated with anhydrous HCl (5 mL), followed by a solution of purified MCPBA (1.1 g, 6.4 mmol) in DMF (10 mL). The reaction mixture was stirred at room temperature for 2½ h, before the DMF was evaporated to dryness under vacuo at 45° C. The residue was dissolved in minimum amount of water (~10 mL) and the product was precipitated from the solution by the dropwise addition of MeOH. The solid was collected and purified by HPLC on a C-18 reverse phase column using 0.5% aqueous AcOH to furnish 0.64 g (45%) of 3: mp 180° C. IR (KBr): 635 (C-Cl), 3100-3400 (NH$_2$,OH) cm$^{-1}$: UV: λ$_{max}$ (pH 1) 260 nm (ε 10,800): λ$_{max}$ (pH 7) 262 nm (ε 10,400): λ$_{max}$ (pH 11) 261 nm (ε 10,000): $^1$H NMR (Me$_2$SO-d$_6$): δ 5.86 (d, 1, $J_{1',2'}$=6.0 Hz, C$_{1'}$H), 7.50 (br s, 2, NH$_2$) and 8.16 (s, 1, C$_2$H).

Method B

Adenosine 5'-monophosphate monohydrate (3.11 g, 8.5 mmol), NaCl (3.11 g, 53 mmol) and NCS (3.33 g, 25 mmol) were dissolved in 50% aqueous AcOH (100 mL) and the solution was stirred at room temperature for 5 days. Evaporation of the reaction mixture and purification of the residue by HPLC on a C-18 reverse phase column using 0.5% aqueous AcOH gave 2.30 g (60%) of the title compound, which was identical to 3 prepared by Method A.

EXAMPLE 4

8-Chloroadenosine 3',5'-cyclic phosphate (4)

Method C

A mixture of dry 8-bromo-cAMP (20 g, 49 mmol) and CaCl$_2$ (20 g, 180 mmol, dried at 75° under vacuum overnight) in anhydrous DMF (800 mL, distilled over CaH$_2$ under vacuum) was heated at 80°-85° C. under anhydrous conditions with stirring for 15 h. DMF was evaporated under reduced pressure at 50° C. and the residue was dissolved in cold 2N NaOH (20 mL). The aqueous solution was neutralized (to pH 7) with cold 2N HCl, filtered through a membrane filter and purified by preparative HPLC on a C-18 reverse phase column. Initial washing with 0.5% AcOH/H$_2$O gave 8-hydroxy-cAMP and cAMP. Further elution with 15% MeOH/H$_2$O gave pure title compound. Evaporation of the solvent gave while solid, which was collected, washed with cold water followed by EtOH and dried to furnish 14.0 g (79%) of 4, mp 232°-234° C.: IR (KBr): 655 (C-Cl) cm$^{-1}$: UV: λ$_{max}$ (pH 1) 260 nm (ε 15,600): λ$_{max}$ (pH 7) 261 nm (ε 15,700): λ$_{max}$ (pH 11) 261 nm (ε 15,900): $^1$H NMR (Me$_2$SO-d$_6$): δ 4.13 (m, 2, C$_{5'}$H$_2$), 4.56-4.39 (m, 1, C$_{4'}$H), 4.99-4.97 and 5.17-5.13 (m, 2, C$_{2'}$H and C$_{3'}$H), 5.85 (s, 1, C$_1$H), 7.67 (br, s, 2, NH$_2$) and 8.21 (s, 1, C$_2$H). Anal. Calcd for C$_{10}$H$_{11}$ClN$_5$O$_6$P.H$_2$O: C, 31.47: H, 3.43: N, 18.53: Cl, 9.29. Found: C, 31.69: H, 3.19: N, 18.26: Cl, 9.52.

Method A

To a solution of adenosine 3',5'-cyclic phosphate (1.15 g, 3.5 mmol) in dry DMF (75 mL, distilled over CaH$_2$) is added dropwise a solution of DMF saturated with anhydrous HCl (5mL), followed by a solution of purified MCPBA (1.1 g, 6.4 mmol) in DMF (10 mL). The reaction mixture is then stirred at room temperature for 2½ h, before the DMF is evaporated to dryness under vacuo at 45° C. The residue is then dissolved in minimum amount of water (~10 mL) and the product precipitated from the solution by the dropwise addition of MeOH. The solid is then collected and purified by HPLC on a C-18 reverse phase column using 0.5% aqueous AcOh to furnish 4, identical to 4 prepared by Method C.

Method B.

To a solution of cAMP (30.3 g, 92 mmol) and NaCl (30.6 g, 52 mmol) in AcOH (250 mL) and H$_2$O (150 mL) was added NCS (30.3 g, 227 mmol). The reaction mixture was stirred at room temperature for 3 days. The solvents were evaporated to dryness under reduced pressure and the residue purified as described above in Method A to yield 13.0 g (39%) of 4, which was identical to 4 prepared by Method C.

EXAMPLE 5

8-Chloroinosine 3',5'-cyclic phosphate (5)

To a suspension of 8-chloroadenosine 3',5'-cyclic phosphate (4, 1.0 g, 2.7 mmol) in H$_2$O (3 mL) was added 2N NaOH dropwise until a clear solution was obtained. NaNO$_2$ (1.05 g, 15 mmol) was added to the reaction solution, followed by dropwise addition of ACOH (2 mL). The reaction mixture was stirred at room temperature overnight and then evaporated to dryness under reduced pressure at 35° C. The residue was purified on a Dowex 50×2-200 (H$^+$) resin column (5×30 cm) eluting with H$_2$O. The homogeneous fractions containing 8-chloro-cIMP were pooled and evaporated to dryness. Co-evaporation of the residue with EtOH (3×25 mL) gave a white solid, which after drying at 78° C. under vacuum for 15 h afforded 0.56 g (56%) of 5: mp 216°-218° C.: IR (KBr): 785 (C-Cl), 1680 (C=O), 3200-3400 (OH) cm$^{-1}$: UV: λ$_{max}$ (pH 1) 251 nm (ε 17,100): λ$_{max}$ (pH 7) 251 nm (ε 17,000): λ$_{max}$ (pH 11) 255 nm (ε 17,300): $^1$H NMR (Me$_2$SO-d$_6$): δ 5.85 (s, 1, C$_{1'}$H), 8.17 (s, 1, C$_2$H), and 12.71 (br s, 1, N$_1$H), 8.17 (s, 1, C$_2$H), and 12.71 (br, s, 1, N$_1$H). Anal. Calcd for C$_{10}$H$_{10}$ClN$_4$O$_7$P): C, 32.94: H, 2.76: N, 15.37. Found: C, 32.75: H, 2.69: N, 15.14.

For utilizing in pharmaceutical preparations of the invention normally a salt of the 3',5'-cyclic phosphate moiety of 8-chloroadenosine 3',5'-cyclic phosphate would be utilized and would be suitably given to a host as a solution in a suitable carrier. Alternately, the free acid form of the compound could be utilized.

Acceptable salts of the phosphate moiety can be selected from, but not necessarily limited to the group consisting of alkali and alkaline earths, e.g. sodium, potassium, calcium, magnesium, lithium, or ammonium and substituted ammonium, trialklyammonium, dialkylammonium, alklyammonium, e.g. triethylammonium, trimethylammonium, diethylammonium, octylammonium, cetyltrimethylammonium and cetylpridium. Such a salt would preferredly be chosen from the group consisting of alkali metal salt, as for instance, a sodium or a potassium salt or an ammonium salt.

In performing the invention, 8-chloroadenosine 3',5'-cyclic phosphate, as a free acid or as a salt, is appropriately mixed with a suitable pharmaceutical carrier which, since the compounds of the invention are water soluble, may be as simple as sterilized water or could be a complex carrier having appropriate agents to suitably mimic certain biological environmental, i.e. pH or salt adjusted for solution suitable for intravenous, intramuscular or other injections.

In selecting a suitable pharmaceutical carrier, consideration of the type of tumor, the site of the tumor and the health and age of the host would be given. 8-Chloroadenosine 3',5'-cyclic phosphate might be appropriately used in the presence of a suitable buffer or as a salt as discussed above. The compounds of the invention are especially useful in treating carcinoma. Included in such a class are mammary, colon, bladder, lung, prostate, stomach and pancreas carcinoma. The treatment method is effective in bringing about regression, palliation, inhibition of growth, and remission of tumors.

Preferredly, 8-chloroadenosine 3',5'-cyclic phosphate of the invention or a salt thereof would be mixed with an appropriate pharmaceutical carrier such that 8-chloroadenosine 3',5'-cyclic phosphate would be suitably soluble in the carrier. Alternately, however, suspensions, emulsions and other formulations of 8-chloroadenosine 3',5'-cyclic phosphate of the invention could be used where indicated. The pharmaceutical carrier, in addition to having a solubilizing or suspending agent therein, might also include suitable dilutants, buffers, surface active agents and other similar agents as are typically used in pharmaceutical carriers. The total composition of the pharmaceutical carrier would, however, be chosen to be compatible with the site of delivery, the concentration of the active ingredient and other parameters as are standard in pharmaceutical industry.

8-Chloroadenosine 3',5'-cyclic phosphate of the invention would be suitably admixed with the pharmaceutical carrier such that it would be present in a concentration of at least 0.1 percent by weight of the total composition. Preferredly, it would be present in the pharmaceutical carrier at a concentration of about 10% to about 90% by weight of the total composition.

Based on present studies, effective amounts of 8-chloroadenosine 3',5'-cyclic phosphate typically would range from about 13 milligrams per kilogram per day (mg/kg/day) of the total body weight of the treated warm blooded animal to about 288 mg/kg/day. Preferredly, the range would by from 22 ml/kg to about 173 mg/mg/day. As with other factors noted above, the amount of 8-chloroadenosine 3',5'-cyclic phosphate utilized in treating an afflicted animal would take into account parameters such as the type of tumor, the tumor site, the form of administering and the physical size and condition of the host. In any event, the actual amount should be sufficient to provide a chemotherapeutically effective amount of the agent in the host in a convenient volume, which will be readily within the ability of those skilled in the art to determine given the disclosure herein.

The 8-chloroadenosine 3',5'-cyclic phosphate of the invention can be given as single doses or as multiple doses divided into sub-doses given daily or over a period of days. As will be evident from the examples below, 8-chloroadenosine 3',5'-cyclic phosphate of the invention exhibits certain inhanced responses when administered as an infusion and, as such, this will be taken in to account in the optimization of a dosage schedule as is well within the skill of the Art given the disclosure herein.

The following examples are given for use of 8-chloroadenosine 3',5'-cyclic phosphate of the invention as a therapeutic agent against neoplastic diseases. In these examples of efficacy of 8-chloroadenosine 3',5'-cyclic phosphate as an antitumor agent is demonstrated by using standard tests against certain malignant tumors.

These standard tests utilize protocols developed under the auspices of the Developmental Therapeutic Program, Division of Cancer Treatment, National Cancer Institute, Bethesda, Maryland, as set forth in *In Vitro Cancer Models*, National Institute of Health Publications No 84-2635, February 1984, United States Department of Health and Human Services, Public Health Service, National Institute of Health.

Staging, growth and testing of tumors was done as is set forth in this publication. The mode of administration and delivery of 8-chloroadenosine 3',5'-cyclic phosphate, however, deviated slightly from these protocols and is as is set forth in each individual example. Evaluation protocols with respect to activity of 8-chloroadenosine 3',5'-cyclic phosphate as an anti-tumor agent, however, follow the criteria as is defined in the above referenced publication.

For the purposes of these examples certain standard abbreviations are utilized as follows: i.p. - intraperitoneal: qd - once a day: and mg/kg/day - milligrams per kilograms per day.

In this example utilizing L1210 as the test tumor cell line, the test results are indicated as % T/C. According to protocols of the National Cancer Institute for the L1210 tumor line, a value greater than 125% is considered as having statically meaningful activity. For test against solid human tumor cell lines, test results are given as change in mean tumor weight. This is expressed in two ways. If there was an increase in tumor weight the results are expressed as $\Delta T/\Delta C$. However, if there was a net negative change in tumor weight the results are expressed as $\Delta T/T$. These two ways of data expressions again follow the protocols and criteria set forth as noted above by the National Cancer Institute.

EXAMPLE 6

8-chloroadenosine 3',5'-cyclic phosphate as a sodium salt was tested utilizing non-tumor bearing $BDF_1$ mice to establish a lethal toxicity for this drug. For this test the drug was delivered i.p. by a bolus injection given as a single dose on day 1. As is evident from Table 1 below, at 104 milligrams per kilograms per injection there were no toxic deaths. At a level of 173 milligrams per kilograms per injection there was a 40 percent toxic death and at 288 milligrams per kilograms per injection the compound exhibited 100 percent lethal toxicity. As will be evident in example 6 below, when the compound is delivered by infusion, the test animals tolerated a higher dose of drug before lethal toxicity was seen.

TABLE 1

Influence of 8-Cl-cAMP Na+ on the life span of non-tumor BDF$_1$ mice when delivered i.p. by bolus injection

| Dosage mg/kg/inj | Route and schedule of delivery | Toxic deaths[1] No killed/No treated |
|---|---|---|
| 480 | ip: qd, day 1 | 5/5 |
| 28 | ip: qd, day 1 | 5/5 |
| 173 | ip: qd, day 1 | 2/5 |
| 104 | ip: qd, day 1 | 0 |
| 62 | ip: qd, day 1 | 0 |
| 37 | ip: qd, day I | 0 |
| 22 | ip: qd, day 1 | 0 |

[1]When delivered qd. day 1 to non-tumor BDF$_1$ mice, the 480 and 288 mb/kg dosages of 8-Cl-cAMP Na+ were lethally toxic for all treated mice. The 173 mg/kg dosage killed 2 of 5 mice and lower dosages were not lethally toxic.

EXAMPLE 7

The activity of 8-chloroadenosine 3′,5′-cyclic phosphate against L1210 inoculated BDF$_1$ mice was determined by both bolus injection and by infusion. As shown in Table 2 below, when delivered by bolus injection there was insignificant activity, however, when infused into a test animal in a dose range of from 22 mg to 173 mg/kg/day, 8-chloroadenosine 3′,5′-cyclic phosphate exhibited significant antitumor activity. Further, the toxicity was determined for the infusion test animals. As is also evident from Table 2 when infused at 173 mg/kg/day the compound was not toxic, however, when infused at the 288 mg/kg/day level both activity and toxicity are noted and at higher levels at 480 and 800 mg/kg/day, the compound is lethally toxic.

The results of Table 2 indicate that 8-chloroadenosine 3′,5′-cyclic phosphate is an effective antitumor agent against L1210 inoculated mice when infused into the test animals. Further the compound demonstrated a dose response for this activity. As was indicated above, a T/C of greater than 125 indicates significant activity.

TABLE 2

Influence of 8-Cl-cAMP Na+ on the postinoculation lifespan of L1210-inoculated BDF$_1$ mice[1] when infused or delivered by bolus injection

| Dosage (mg/kg/day) | Route and schedule of delivery | Postinoculation lifespan[2] (T/C) |
|---|---|---|
| 104 | ip: qd, day 1–7 | 98 |
| 62 | ip: qd, day 1–7 | 103 |
| 37 | ip: qd, day 1–7 | 93 |
| 22 | ip: qd, day 1–7 | 103 |
| 800 | ip: 24-hr infusion, day 1–5 | 62 toxic[3] |
| 480 | ip: 24-hr infusion, day 1–5 | 93 toxic[3] |
| 288 | ip: 24-hr infusion, day 1–5 | 128 toxic[3] |
| 173 | ip: 24-hr infusion, day 1–5 | 131 |
| 104 | ip: 24-hr infusion, day 1–5 | 137 |
| 62 | ip: 24-hr infusion, day 1–5 | 137 |
| 37 | ip: 24-hr infusion, day 1–5 | 126 |
| 22 | ip: 24-hr infusion, day 1–5 | 126 |
| 13 | ip: 24-hr infusion, day 1–5 | 113 |
| 48 | ip: 24-hr infusion, day 1–5 | 100 |
| 17 | ip: 24-hr infusion, day 1–5 | 100 |
| 0.6 | ip: 24-hr infusion, day 1–5 | 100 |

[1]Mice were inoculated i.p. with $1 \times 10^6$ cells of murine leukemia L1210 24-hr before first treatment. Each treatment group consisted of 5 mice. Twenty control mice that received a 0.9% solution of NaCl lived $6.2 \pm$ days.
[2]Significant activity indicated at T/C > 125.
[3]When infused, the 800 and 480 mg/kg dosages of 8-Cl-cAMP Na+ were lethally toxic for all treated mice while the 288 mg/kg dosage killed 2 of 5 mice.

8-chloroadenosine 3′,5′cyclic phosphate was tested against a variety of solid human tumor cell lines. In the tests of examples 8 through 11 shown in Tables 3 through 6, what is being measured is tumor regression size and not increase in life span of the test animal. This expression follows the accepted Nation Cancer Institute protocol procedures for respective solid tumors cell lines which were tested.

EXAMPLE 8

In this example, 8-chloroadenosine 3′,5′-cyclic phosphate given by infusion was tested against human mammary carcinoma in athymic mice. In a first study shown in the upper portion of Table 3a at the dose levels given there was a mean reduction in tumor weight. As such the change in this means reduction in tumor weight, following the Nation Cancer Institute protocols as noted above, is expressed as ΔT/T. In the study shown in the lower portion of Table 3a, at lower dose levels, the Δ weight between the starting tumor weight and the final tumor weight was greater than unity and as such again following the established protocols the results are shown as ΔT/ΔC.

Any value for ΔT/ΔC or ΔT/T which is below 25 is considered by the National Cancer Institute protocols as indicative of significant activity. As is evident from Table 3a significant activity was indicated over a large dosage range of from 22 mg/kg up to and including 173 mg/kg.

TABLE 3a

Influence of intraperitoneally infused 8-Cl—cAMP Na+ on the growth in athymic mice of human mammary carcinoma MX-1[1]

| Dosage (mg/kg/day) | Initial Mean Weight (mg) | Δ First-Last Tumor Weight[2] | Change in Mean Tumor Weight[3] (ΔT/ΔC or ΔT/T) |
|---|---|---|---|
| 173 | 375 | −39 | −10.4[4] |
| 104 | 346 | −23 | −6.7[4] |
| 62 | 337 | −49 | −14.5[4] |
| 0 | 334 | 215 | — |
| 37 | 194 | 16 | 6[5] |
| 22 | 201 | 76 | 29[5] |
| 13 | 216 | 95 | 37[5] |
| 0 | 204 | 259 | — |

[1]Tumor fragments (~14 mg) were implanted subcutaneously in the thigh region of athymic CD-1 female mice. Three weeks later the tumors were staged and treatment lasting 7 days was started, each treatment group consisted of 7 mice.
[2]Tumor measurements recorded on the initial day of treatment (staging day) and again on day 8 were used to calculate mean tumor weight changes and ΔT/ΔC or ΔT/T.
[3]ΔT/ΔC utilized for positive First-Last tumor weights and ΔT/T utilized for negative First-Last tumor weights.
[4]ΔT/T
[5]ΔT/ΔC The mean tumor weight at each dose shown in Table 3a for all the test animals at days 1 and 8 are indicated in Table 3b.

TABLE 3b

Tumor weights of human mammary carcinoma MX-1[1] tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 173 | 375 | 336 |
| 104 | 346 | 317 |
| 62 | 337 | 288 |
| control | 334 | 549 |
| 37 | 194 | 210 |
| 22 | 201 | 277 |
| 13 | 216 | 311 |
| control | 204 | 463 |

EXAMPLE 9

8-chloroadenosine 3',5'-cyclic phosphate was further tested in athymic mice against human colon carcinoma LoVo. As per example 8, administration was also by infusion. The results of this test are shown in Table 4a below. The mean change in tumor weight is indicated either as ΔT/ΔC for the positive value or ΔT/T for the negative values as was discussed with respect to Example 8 above. As is evident at the 37 and 62 kg/mg dosage the compound exhibited significant activity.

TABLE 4a

Influence of intraperitoneally infused 8-Cl-cAMP Na+ on the growth in athymic mice of human colon carcinoma LoVo[1]

| Dosage (mg/kg/day) | Initial Mean Weight (mg) | Δ First-Last Tumor Weight[2] | Change in Mean Tumor Weight (ΔT/ΔC or ΔT/T) |
|---|---|---|---|
| 104 | 288 | 29 | 35[4] |
| 62 | 293 | −3 | 1.0[5] |
| 37 | 288 | −4 | 1.4[5] |
| 0 | 292 | 84 | — |

[1]Tumor fragments (~14 mg) were implanted subcutaneously in the thigh region of athymic CD-1 female mice. Three weeks later the tumors were staged and treatment lasting 7 days was started, each treatment group consisted of 7 mice.
[2]Tumor measurements recorded on the initial day of treatment (staging day) and again on day 8 were used to calculate mean tumor weight changes and ΔT/ΔC or ΔT/T.
[3]ΔT/ΔC utilized for positive First-Last tumor weights and ΔT/T utilized for negative First-Last tumor weights.
[4]ΔT/ΔC
[5]ΔT/T The mean tumor weight for each dose shown in Table 4a for all the test animals at days 1 and 8 are indicated in Table 4b.

TABLE 4b

Tumor Weights of human colon carcinoma LoVo[1] tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 104 | 288 | 317 |
| 62 | 293 | 290 |
| 37 | 288 | 284 |
| control | 292 | 376 |

EXAMPLE 10

8-chloroadenosine 3',5'-cyclic phosphate was further tested in athymic mice against human mammary carcinoma MDA-MB-231. The test was also done using infusion as the route of administration. The results of this test are shown in Table 5a below. The compound exhibited significant activity at the dose levels of 62 and 104 mg/kg/day. Further while it did not exhibit significant activity at all dose levels it did show a linearity of response throughout the tested dosage range against this tumor line.

TABLE 5a

Influence of intraperitoneally infused 8-Cl-cAMP Na+ on the growth in athymic mice of human mammary carcinoma MDA-MB-231[1]

| Dosage (mg/kg/day) | Initial Mean Weight (mg) | Δ First-Last Tumor Weight[2] | Change in Mean Tumor Weight[3] ΔT/ΔC |
|---|---|---|---|
| 104 | 367 | 66 | 18 |
| 62 | 375 | 96 | 26 |
| 37 | 367 | 149 | 41 |
| 0 | 361 | 365 | — |

[1]Tumor fragments (~14 mg) were implanted subcutaneously in the thigh region of athymic CD-1 female mice. Three weeks later the tumors were staged and treatment lasting 7 days was started, each treatment group consisted of 7 mice.
[2]Tumor measurements recorded on the initial day of treatment (staging day) and again on day 8 were used to calculate mean tumor weight changes and ΔT/ΔC or ΔT/T.
[3]ΔT/ΔC utilized for positive First-Last tumor weights.

The mean tumor weight for each dose shown in Table 5a for all the test animals at days 1 and 8 are indicated in Table 5b.

TABLE 5b

Tumor weights of human mammary carcinoma MDA-MB-231 tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 14 | 367 | 433 |
| 62 | 375 | 471 |
| 37 | 367 | 516 |
| control | 361 | 726 |

EXAMPLE 11

8-chloroadenosine 3',5'-cyclic phosphate was further tested in athymic mice against human lung carcinoma LX1. As per the results shown in Table 6a below, the compound exhibited significant activity at a dose range of from 37 mg to 104 mg/kg/day. For this test infusion was only for 5 days as opposed to the 7 days used for the previous solid tumor tests of Examples 8, 9 and 10. Further, as per Example 8 the positive mean tumor weights results are shown as ΔT/ΔC and negative mean tumor weights as ΔT/T. It is significant to note at 62 and 104 mg dosage range there was a high degree of tumor weight loss as opposed to only inhibition of tumor growth, i.e. at the 62 and 104 mg dose levels there was tumor regression.

TABLE 6a

Influence of intraperitoneally infused 8-Cl-cAMP Na+ on the growth in athymic mice of human lung carcinoma LX-1[1]

| Dosage (mg/kg/day) | Initial Mean Weight (mg) | ΔFirst-Last Tumor Weight[2] | Change in Mean Tumor Weight[3] ΔT/ΔC |
|---|---|---|---|
| 104 | 324 | −54 | −16.7[4] |
| 62 | 327 | −50 | −15.3[4] |
| 37 | 330 | 11 | 6[5] |
| 0 | 332 | 183 | — |

[1]Tumor fragments (~14 mg) were implanted subcutaneously in the thigh region of athymic CD-1 female mice. Three weeks later the tumors were staged and treatment lasting 5 days was started, each treatment group consisted of 7 mice.
[2]Tumor measurements recorded on the initial day of treatment (staging day) and again on day 8 were used to calculate mean tumor weight changes and ΔT/ΔC or ΔT/T.
[3]ΔT/ΔC utilized for positive First-Last tumor weights and ΔT/T utilized for negative First-Last tumor weights.
[4]ΔT/T
[5]ΔT/ΔC The mean tumor weight for each dose shown in Table 6a for all the test animals at days 1 and 8 are indicated in Table 6b.

TABLE 6b

Tumor weights of human lung carcinoma LX-1 tumors in athymic mice intraperitoneally infused with 8-Cl-cAMP Na+

| Dosage (mg/kg/day) | Initial Mean Weight (mg) Day 1 | Mean Tumor Weight (mg) Day 8 |
| --- | --- | --- |
| 104 | 324 | 270 |
| 62 | 327 | 277 |
| 37 | 330 | 341 |
| control | 332 | 515 |

For delivery to a host afflicted with a neoplastic disease 8-chloroadenosine 3',5'-cyclic phosphate of the invention can be formulated in various formulations to prepare pharmaceutical compositions containing 8-chloroadenosine 3',5'-cyclic phosphate of the invention as active ingredients. The following illustrative examples are given for the formulations of such pharmaceutical compositions utilizing the sodium salt of 8-chloroadenosine 3',5'-cyclic phosphate.

In these examples, Pharmaceutical Preparative Example 12 illustrates the use of 8-chloroadenosine 3',5'-cyclic phosphate sodium salt in injectables suitable for intravenous or other types of injection into the host animal. Pharmaceutical Preparative Example 13 is directed to an oral syrup preparation, Pharmaceutical Preparative Example 14 to an oral capsule preparation and Pharmaceutical Preparative Example 15 to oral tablets. Pharmaceutical Preparative Example 16 is directed to use of 8-chloroadenosine 3',5'-cyclic phosphate sodium salt in suitable suppositories. For Pharmaceutical Preparative Examples 12 through 16, the ingredients are listed followed by the methods of preparing the composition.

EXAMPLE 12

| INJECTABLES | |
| --- | --- |
| 8-chloroadenosine 3',5'-cyclic phosphate sodium salt | 20 mg–1000 mg |
| Water for Injection USP q.s. | |

The 8-chloroadenosine 3',5'-cyclic phosphate sodium salt is dissolved in the water and passed through a 0.22μ filter. The filtered solution is added to ampoules or vials, sealed and sterilized.

EXAMPLE 13

| SYRUP 250 mg Active ingredient/5 ml syrup | |
| --- | --- |
| 8-chloroadenosine 3',5'-cyclic phosphate sodium salt | 50.0 g |
| Purified Water USP q.s. or | 200 ml |
| Cherry Syrup q.s. ad | 1000 ml |

The 8-chloroadenosine 3',5'-cyclic phosphate sodium salt is dissolved in the water and to this solution the syrup is added with mild stirring.

EXAMPLE 14

| CAPSULES 100 mg 250 mg or 500 mg | |
| --- | --- |
| 8-chloroadenosine 3',5'-cyclic phosphate sodium salt | 500 g |
| Lactose WSP, Anhydrous q.s. or | 200 g |
| Sterotex Powder HM | 5 g |

Combine the 8-chloroadenosine 3',5'-cylcic phosphate sodium salt and the Lactose in a twin-shell blender equipped with an intensifier bar. Tumble blend for two minutes, followed by blending for one minute with the intensifier bar and then tumble blend again for one minute. A portion of the blend is then mixed with the Sterotex Powder, passed through a #30 screen and added back to the remainder of the blend. The mixed ingredients are then blended for one minute, blended for the intensifier bar for thirty seconds and tumble blended for an additional minute. Appropriate sized capsules are filled with 141 mg, 352.5 mg or 705 mg of the blend, respectively, for the 100 mg, 260 mg and 500 mg containing capsules.

EXAMPLE 15

| TABLETS 100 mg, 200 mg or 500 mg | |
| --- | --- |
| 8-chloroadenosine 3',5'-cyclic phosphate | 500 g |
| Corn Starch NF | 200.0 g |
| Cellulose Microcrystalline | 46.0 g |
| Sterotex Powder HM | 4.0 g |
| Purified Water q.s. or | 300.0 ml |

Combine the corn starch, the cellulose and the 8-chloroadenosine 3',5'-cyclic phosphate together in a planetary mixer and mix for two mintues. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen at medium speed. The Sterotex Powder is added to a portion of the mix and passed thrugh a #30 screen and added back to the milled mixture and the total blended for five minutes by drum rolling. Compressed tables of 150 mg, 375 mg and 750 mg respectively, of the total mix are formed with appropriate sized punches for the 100 mg, 250 mg or 500 mg containing tables.

EXAMPLE 16

| SUPPOSITORIES 20 mg, 500 mg or 100 mg per 3 g | | | |
| --- | --- | --- | --- |
| 8-chloroadenosine 3',5'-cyclic phosphate sodium salt | 250 mg | 500 mg | 1000 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60° C. and dissolve the 8-chloroadenosine 3',5'-cyclic phosphate sodium salt into the melt. Mold this total at 25° C. into appropriate suppositories.

What is claimed is:

1. A process for preparing chloro compounds of the formula

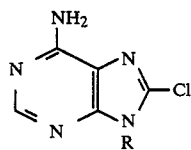

wherein R is H or

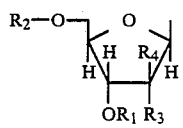

$R_1$ and $R_2$ are H or

or together $R_1$ and $R_2$ are

and $R_3$ and $R_4$ are H or one of $R_3$ or $R_4$ is OH and the other is H, and pharmaceutically acceptable salts thereof which comprises the steps of:

stirring a starting compound of the formula

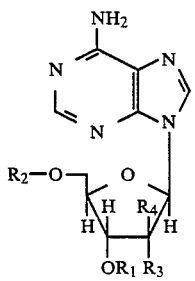

wherein $R_1$ and $R_2$ are H or

or together $R_1$ and $R_2$ are

and $R_3$ and $R_4$ are H or one of $R_3$ or $R_4$ is OH and the other is H, in a solvent with N-chlorosuccinimide and an acid of a strength insufficient to cleave the sugar-heterocycle glycosidic bond of said compound.

2. The process of 1 wherein:
said solvent is chosen from the group consisting of dimethylacetamide, dimethylformamide and aqueous medium.

3. The process of claim 1 wherein:
said acid is an organic acid.

4. The process of claim 3 wherein:
said organic acid is selected from the group consisting of acetic acid and formic acid.

5. The process of claim 1 wherein $R_3$ is OH and $R_4$ is H.

6. The process of claim 5 wherein: $R_1$ and $R_2$ are

or together $R_1$ and $R_2$ are

7. The process of claim 6 wherein: together $R_1$ and $R_2$ are

8. The process of claim 6 wherein:
said starting compound is treated with N-chlorosuccinimide and acetic acid in water.

9. A process of preparing 8-chloroadenosine 3',5'-cyclic phosphate which comprises:
stirring adenosine 3',5'-cyclic phosphate with N-chlorosuccinimide and acetic acid in water.

10. A process of preparing 8-chloroadenosine 3',5-cyclic phosphate which comprises:
stirring adenosine 3',5'-cyclic phosphate, N-chlorosuccinimide, sodium chloride and acetic acid in water.

11. A process of preparing 8-chloroadenosine 3',5'-cyclic phosphate which comprises:
stirring 8-bromoadenosine 3',5'-cyclic phosphate and calcium chloride in a solvent at an elevated temperature;
removing said solvent to yield a residue;
dissolving said residue in a basic solution;
neutralizing said basic solution with an acid;
loading said neutralized solution on a chromatographic column; and
eluting said 8-chloroadenosine 3',5'-cyclic phosphate from said column.

12. The process of claim 11 wherein:
said solvent is dimethylformamide.

* * * * *

UNITED STATES PATENT AND TRADEMARK OFFICE
CERTIFICATE OF CORRECTION

PATENT NO. : 4,861,873
DATED : AUGUST 29, 1989
INVENTOR(S) : ROBINS, ET AL.

It is certified that error appears in the above-identified patent and that said Letters Patent is hereby corrected as shown below:

Column 1, line 21, "confirm" should be --confirmed--.

Column 1, line 28, insert --of-- between "Department" and "Health".

Column 1, line 55, "syntesis" should be --synthesis--.

Column 4, line 9, "conduct" should be --conducted--.

Column 4, line 40, "3',5'-phosphate" should be --3',5'-cyclic phosphate--.

Column 4, line 47, "adensoine" should be --adenosine--.

Column 4, line 53, "dimethylforamide" should be --dimethylformamide--.

Column 7, line 11, "18:1:18" should be --18:1:81--.

Column 7, line 63, "while" should be --white--.

Column 7, line 66, insert --3280($NH_2$, OH)-- between "(C-C1)" and "$cm^{-1}$"--.

Column 8, line 42, "30 cm" should be --20 cm--.

Column 8, lines 52 and 53, delete the second occurrence of "8.17 (s, 1, $C_2H$), and 12.71 (br, s, 1, $N_1H$)".

Column 9, line 55, "ml/kg" should be --mg/kg--.

Column 9, line 56, "mg" (second occurrence) should be --kg--.

UNITED STATES PATENT AND TRADEMARK OFFICE
CERTIFICATE OF CORRECTION

PATENT NO. : 4,861,873
DATED : AUGUST 29, 1989
INVENTOR(S) : ROBINS, ET AL.

It is certified that error appears in the above-identified patent and that said Letters Patent is hereby corrected as shown below:

Column 11, line 7, "28" should be --288--.
Column 11, line 12, "mb/kg" should be --mg/kg--.
Column 12, line 1 and Column 12, line 13, "Nation" should be --National--.
Column 14, line 22, "AMP" should be --cAMP--.
Column 15, line 41, "20 mg" should be --250 mg--.
Column 16, line 20, "260" should be --250--.
Column 16, line 26, "200" should be --250--.
Column 16, line 44 and column 16, line 47, "tables" should be --tablets--.
Column 16, line 52, "20" should be --250--.
Column 16, line 52, "100" should be --1000--.
Column 16, lines 55 and 56, "1925 mg    1750mg    mg
                                              1400     "
    should be --1925 mg    1750 mg    1400 mg--.
Column 16, line 66, "What is claimed is" should be --We claim--.

Signed and Sealed this

Eighth Day of January, 1991

Attest:

HARRY F. MANBECK, JR.

*Attesting Officer*     *Commissioner of Patents and Trademarks*